US006337189B1

(12) United States Patent
Ryan

(10) Patent No.: US 6,337,189 B1
(45) Date of Patent: Jan. 8, 2002

(54) FIXATIVE SYSTEM, METHOD AND COMPOSITION FOR BIOLOGICAL TESTING

(75) Inventor: Wayne L. Ryan, Omaha, NE (US)

(73) Assignee: Streck Laboratories, Inc., La Vista, NE (US)

( * ) Notice: Subject to any disclaimer, the term of this patent is extended or adjusted under 35 U.S.C. 154(b) by 0 days.

(21) Appl. No.: 09/500,248

(22) Filed: Feb. 8, 2000

(51) Int. Cl.$^7$ .................. G01N 1/30; G01N 33/574; G01N 1/28; G01N 31/00; C12Q 1/70
(52) U.S. Cl. .................. 435/40.5; 435/5; 435/7; 435/40.51; 435/40.52; 436/8; 436/18
(58) Field of Search .................. 435/40.51, 40.5, 435/40.52, 5, 7.23; 436/8, 16, 17, 18

(56) References Cited

U.S. PATENT DOCUMENTS

| | | |
|---|---|---|
| 3,546,334 A | 12/1970 | Lerner et al. |
| 4,578,282 A | 3/1986 | Harrison |
| 4,857,300 A | 8/1989 | Maksem |
| 5,104,640 A | 4/1992 | Stokes |
| 5,196,182 A | 3/1993 | Ryan |
| 5,250,438 A | 10/1993 | Ryan |
| 5,256,571 A | 10/1993 | Hurley et al. |
| 5,260,048 A | 11/1993 | Ryan |
| 5,346,811 A * | 9/1994 | Galindo-Castro et al. ...... 435/5 |
| 5,432,056 A | 7/1995 | Hartman et al. |
| 5,459,073 A | 10/1995 | Ryan |
| 5,460,797 A | 10/1995 | Ryan |
| 5,811,099 A | 9/1998 | Ryan |
| 5,849,517 A | 12/1998 | Ryan |

OTHER PUBLICATIONS

William Check, PHD, "Finding the Proper Fit for Pap Smear Devices," Cap Today, p. 18, (Dec. 1998).
Allen, "A Guide to Cytopreparation," Am. Soc. for Cytotechology.
J.R. Baker, "Principles of biological microtechnique: a study of fixation and dyeing," New York, Barnes & Noble, Inc., pp. 19–65 (1959).
J. Ben–Ezra et al., "Effect of fixation on the amplification of nucleic acids from apraffin–embedded material by the polymerase chain reaction," J. Histochem. Cytochem., Cytochem., vol 39, p. 351, (1991).
L.D. Bourne, "Gynaecological Cytology," Theory and Practice of Histological Techniques, Church Hill Livingstone, Edinburgh, (1990).
R.M. Briggs, "Dysplasia and Early Neoplasia of the Uterine Cervix: A review," Obstet. Gynecol. Surv., vol. 34, pp. 70–99.
K.L. Chua and A. Hjerpe, "Polymerase Chain Reaction Analysis of Human Papilomavirus in Archival Cervical Cytology Smears," AQCH, vol. 17 (No. 4), pp. 221–228, (1995).

D.D. Davey, et al., "Atypical Squamous Cells of Undetermined Significance: Interlaboratory Comparisons and Quality Assurance Monitors," Diag. Cytopathol., vol. 11, pp. 390–396, (1994).
R.M. Demay, "Problems in Pap Smear Interpretation," Arch. Pathol. Lab Med., vol. 121, 99. 229–238, (1997).
David Hopwood, "Fixation and Fixatives in Theory and Practice of Histological Techniques," Church Hill Livingstone, Endinburgh, (1990).
W.K. Kinney, et al., "Where's the High Grade Cervical Neoplasia? The Importance of Minimally Abnormal Papanicolaou Diagnosis", Obstet. Gynecol., vol. 91, pp. 973–976, (1998).
L.G. Koss, "The Papanicolaou Test for Cervical Cancer Detection: A Triumph and a Tradegy," JAMA, pp. 737–743, (1989).
K. Nasiell et al., "Behavior of Mild Cervical Dysplasias During Long–Term Follow–Up", Obstet. Gynecol., vol. 67, pp. 665–669, (1986).
National Cancer Inst. Workshop, "The Revised Bethesda System for Reporting Cervical/Vaginal Diagnosis: Report of the 1991 Bethesda Workshop", JAMA, vol. 267, pp. 1092 (1992).
G. J. Nuovo and R.M. Richart, "Buffered formalin is the superior fixative for the detection of HPV DNA by in situ hybridization analysis", Am. J. Pathol., vol. 134, p. 837 (1989).
H. Tanaka et al., "Patients with various types of human papillomavirus," Cytopath., vol. 4, pp. 273–283, (1993).
L.M. Weiss and Y.Y. Chen, "Effects of different fixatives on detection of nucleic acids from paraffin–embedded tissues by in situ hybridization using oligonucleotide probes," J. Histochem. Cytochem., vol. 39, pp. 1237 (1991).
J.H. Williams et al., "Tissue preparation for immunocytochemistry," J. Clin. Pathol., vol. 50, p. 442, (1997).
McDonald et al., "Use of the Same Archival Papanicolaou Smears for Detection of Human Papillomavirus by Cytology and Polymerase Chain Reaction," Diagnostic Molecular Pathology, vol. 8 (No. 1), pp. 20–25, (1999).
Surgipath Cytology Fixative Packaging (3 sheets).
McClatchey, Kenneth, et al., "Nongyneocologic Cytologic Specimens: Collection and Cytopreparatory Techniques; Approved Guideline," NCCLS, vol. 19, No. 14, Replaces GP23–P (Aug. 1999).
Hayat, M.A., "Fixation for Electron Microscopy," Academic, pp. 1–5, Press 1981.
Jones, Bruce A., et al., "Gynecologic Cytology Turnaround Time, A College of American Pathologists Q–Probes Study of 371 Laboratories," Arch Pathol Lab Med, vol. 123, pp. 682–686 (1999).

* cited by examiner

*Primary Examiner*—James Housel
*Assistant Examiner*—Shanon A. Foley
(74) *Attorney, Agent, or Firm*—Dobrusin & Thennisch PC

(57) ABSTRACT

A system, composition and method for the stabilization of biological specimens, which employs a chemical fixative.

34 Claims, No Drawings

FIXATIVE SYSTEM, METHOD AND COMPOSITION FOR BIOLOGICAL TESTING

TECHNICAL FIELD

The present invention relates generally to biological specimen fixatives and more particularly to a fixative for preserving a specimen for serial or archival diagnostic examinations.

BACKGROUND ART

Exfoliative cytology is the study of cells, either naturally shed or collected, from a tissue surface. The importance of cytology as a diagnostic tool lies in the knowledge that any changes in these superficial cells can be a reflection of changes in the immediate underlying tissue. For example, the role of cytology in the field of gynecology has three important applications: (1) the detection of malignant lesions, (2) the assessment of hormone function, and (3) the identification of vaginal infections. The detection of malignant changes as early as possible in its genesis bears a direct relationship to the prognosis.

Thus, for instance, the examination of asymptomatic women for the early detection of carcinoma of the cervix is of prime importance. Carcinoma in situ is a malignant change in the cervical epithelium leaving the basement membrane unviolated, i.e., it is non-invasive. Endometrial carcinoma can also be detected cytologically, as can malignancies of the fallopian tubes, ovaries, vagina and vulva.

Diagnostic cytology has been used extensively as a detection system for alterations in cellular morphology, such as alterations which may occur when a normal cell develops into a cancerous cell. One of the main applications of diagnostic cytology is in the early detection of cervical cancer. The cervical smear and staining technique was developed by George N. Papanicolaou for detection of early neoplastic changes in the uterine cervix. In its current form, it is a necessary routine and major screening procedure for women of all ages. As such, the test has become a convenient focus for the medical profession to regularly review the health status of American women. The modem Papanicolaou ("Pap") screening technique, is the most successful test developed for reducing the incidence of cancer of the uterine cervix.

The success rate of this screening technique is influenced by such factors as the clinical sensitivity of the screening method, that is, the false negative rate attributed by errors during sampling, screening and evaluation. In practice, although a remarkable reduction in cervical cancer has in fact occurred, this cancer has never been completely eradicated in any population ever reported, no matter how thoroughly screened. Koss, L. G. (1989), The Papanicolaou Test for Cervical Cancer Detection: A Triumph and a Tragedy, JAMA 261:737–743; see also DeMay, "Problems in Pap Smear Interpretation", Arch. Pathol. Lab. Med. 121:229–23 (1997).

The quality of the Papanicolaou screening in the United States has received significant attention in both the public and professional sectors over the past few years. This attention has resulted in increased interest and effort from professional societies, regulatory agencies, and industry to address concerns and propose mechanisms to improve and insure the effectiveness, reliability and accuracy of the Pap screening technique. In this regard, recognition of etiologic factors in the development of cervical cancer, for example human papillomavirus (HPV) infections, may improve the sensitivity of screening programs. Morphologic assessment of such infections has potential drawbacks ("Buffered formalin is the superior fixative for the detection of HPV DNA by in situ hybridization analysis." Am. J. Pathol. 134:837; Tanaka, H., et al. (1993), "Patients with various types of human papillomavirus" Cytopath. 4:273–283), with it being recognized that a sensitive method of detection would be of particular value. Chua and Hjerpe, "Polymerace Chain Reaction of Human Papillomavirus in Archival Cervical Cytology Smears," AQCH 17(4):221–228 (1995).

Currently, the primary purpose of obtaining a specimen of cells from the cervix is for use in cytopathology to detect cervical cancer, its precursors, and other abnormalities of the reproductive tract. It would be desirable to use a sample slide preparation, such as collected for conventional cervical carcinoma cytologic screening, to perform ancillary studies to detect alterations in DNA or protein associated with carcinogenesis. A method which simultaneously permits rapid tissue fixation, excellent morphologic detail, antigen preservation without masking or denaturation, and/or which results in less RNA and DNA degradation would, therefore, be highly desirable in the diagnosis of gynecological pathologies. As those of skill in the art recognize, the specimen to be tested must also be immobilized so that it will not be damaged or released during transport for processing or during the rigorous assay procedures associated with immunocytochemical and molecular procedures.

These procedures commonly are performed on embedded or frozen tissue biopsies. Fixative type and fixation time are known to influence not only the preservation of tissue morphology (Baker, "Principles of Biological Microtechnique: A Study of Fixation and Dyeing," 1959) and the preservation of protein antigens for immunocytochemistry (Williams, J. H., et al. (1997), "Tissue preparation for immunocytochemistry." J Clin. Pathol. 50:422), but also the preservation of nucleic acids for in situ hybridization ("Patients with various types of human papillomavirus" Cytopath. 4:273–283; Weiss, L. M., and Chen, Y. Y. (1991), "Effects of different fixatives on detection of nucleic acids from paraffin-embedded tissues by in situ hybridization using oligonucleotide probes."; "The Revised Bethesda System for Reporting Cervical/Vaginal Diagnosis: Report of the 1991 Bethesda Workshop." JAMA 267:1092; Nuovo, G. J., and Richart, R. M. (1989), "Buffered formalin is the superior fixative for the detection of HPV DNA by in situ hybridization analysis." Am. J. Pathol. 134:837; and in situ amplification (Ben-ezra, et al., Effect of Fixation on the Amplification of Nucleic Acids from Paraffin-Embedded Material by the Polymerase Chain Reaction," J. Histochem. Cytochem. 39:351 (1991)).

The process of fixation forms the foundation for the evaluation of biological specimens on slides and for the preparation of tissue sections. For most applications, fixation preferably should prevent or arrest autolysis and putrefaction, preserve antigenic sites, preserve morphology, stabilize DNA, RNA and soluble and structural proteins, fortify the tissues against the deleterious effects of subsequent processing and facilitates staining, or a combination of some or all of these features. Biological specimens are analyzed for many purposes using a variety of different assays, including diagnostic cytology, immunocytochemistry and molecular pathology. Current methods of fixation rely on chemical agents, the most widely used being formaldehyde and alcohol.

Examples of efforts in this field include conventional aqueous bi-sulfite-based fixatives (with acetic buffer), PVP-based fixatives (with propylene glycol and methanol) as well as those outlined in U.S. Pat. No. 3,546,334 (Lerner); U.S. Pat. Nos. 4,578,282; 4,857,300 (Maksem); U.S. Pat. No. 5,104,640 (Stokes); U.S. Pat. No. 5,256,571 (Hurley); and U.S. Pat. No. 5,432,056 (Hartman et al), all of which are hereby expressly incorporated by reference. One particularly effective formulation is disclosed in U.S. Pat. No. 5,196,182 (Ryan). An example of a commercially available product is that offered by Surgipath Medical Industries, Inc. (Richmond, Ill.) under the name SURGIPATH Cytology Fixative. The latter contains ethanol, polyethylene glycol and distilled water. The polyethylene glycol generally provides a waxy coating to stop evaporation, which requires removal before slide staining. Other common exfoliative cytology fixatives include additives such as glacial acetic acid (e.g. at 3%).

In recent years, the U.S. Food and Drug Administration has approved new devices for gynecological screening, as discussed in "Finding the Proper Fit for Pap Smear Devices", by William Check, PhD, CAP TODAY (December 1998), pp. 18 et seq, hereby incorporated by reference. With the advancement in such testing there has been a more acute recognition of the long felt need for improved specimen preparation techniques.

In accordance with the above discussion, background literature of potential interest as to the present invention includes: Allen, "A Guide to Cytopreparation," Am. Soc. for Cytotechnology; Baker, J. R. (1959), "Principles of biological microtechnique: a study of fixation and dyeing," New York, Barnes & Noble, Inc.; Ben-ezra, J., et al. (1991), "Effect of fixation on the amplification of nucleic acids from paraffin-embedded material by the polymerase chain reaction," J. Histochem. Cytochem. 39:351; Bourne, L. D. (1990), *Theory and Practice of Histological Techniques,* "Gynaecological Cytology," Church Hill Livingstone, Edinburgh; Briggs, R. M. (1979), "Dysplasia and Early Neoplasia of the Uterine Cervix: A Review," Obstet. Gynecol. Surv. 34:70–99; Chua, K. L., and Hjerpe, A. (1995). "Polymerace chain reaction of human papillomavirus in Archival Cervical cytology smears," AQCH 17(4):221–228; Davey, D. D., et al. (1994), "Atypical Squamous Cells of Undetermined Significance: Interlaboratory Comparisons and Quality Assurance Monitors," Diag. Cytopathol. 11:390–396; DeMay, R. M. (1997). "Problems in Pap Smear Interpretation," Arch. Pathol. Lab Med. 121:229–238; Hopwood, David (1990), "Fixation and Fixatives in Theory and Practice of Histological Techniques," Churchill Hill Livingstone, Edinburgh; Kinney, W. K., et al. (1998) "Where's the High Grade Cervical Neoplasia? The Importance of Minimally Abnormal Papanicolaou Diagnosis." Obstet. Gynecol. 91:973–976; Koss, L. G. (1989), The Papanicolaou Test for Cervical Cancer Detection: A Triumph and a Tragedy, JAMA 261:737–743; Nasiell, K., et al. (1986), "Behavior of Mild Cervical Dysplasias During Long-Term Follow-up." Obstet. Gynecol. 67:665–669; National Cancer Inst. Workshop (1992), "The Revised Bethesda System for Reporting Cervical/Vaginal Diagnosis: Report of the 1991 Bethesda Workshop." JAMA 267:1092; Nuovo, G. J., and Richart, R. M. (1989), "Buffered formalin is the superior fixative for the detection of HPV DNA by in situ hybridization analysis." Am. J. Pathol. 134:837; Tanaka, H., et al. (1993), "Patients with various types of human papillomavirus" Cytopath. 4:273–283; Weiss, L. M., and Chen, Y. Y. (1991), "Effects of different fixatives on detection of nucleic acids from paraffin-embedded tissues by in situ hybridization using oligonucleotide probes." J. Histochem. Cytochem. 39:1237; and Williams, J. H., et al. (1997), "Tissue preparation for immunocytochemistry." J. Clin. Pathol. 50:422. All of the above-cited publications are hereby expressly incorporated by reference.

SUMMARY OF THE INVENTION

The present invention overcomes the shortcomings of the prior art by providing an improved composition and system for the preservation of biological test specimens. The specimens are preserved in a fixative medium that offers one or more advantages such as rapid cell or tissue penetration, minimal specimen shrinkage, protein preservation, antigen preservation, morphology preservation, stain permeability, lysis of pathogens or the like. Moreover, the medium permits effective adhesion to specimen mounting surfaces such as glass slide surfaces. Use of the composition and system of the present invention thus affords a generally long term record of the specimen, making it attractive for archiving and multiple testing, without the need for obtaining further samples from the test subject.

In accordance with the present invention, there is provided a system, method and composition for the preservation of biological test specimens which includes the use of an effective amount of a chemical fixative dispersed in a liquid medium (e.g., a non-crosslinking fixative). In a particularly preferred embodiment, the chemical fixative includes a urea containing reaction product (e.g., a heterocyclic urea) of a reaction involving an aldehyde (e.g., formaldhyde with allantoin), and more preferably, includes up to about 5% of the same in a medium that is substantially free of water. The system of the present invention contemplates the use of the composition of the present invention for preservation of cell samples, tissue samples, or both, for cyto-pathological examination. Thus, contemplated as within the scope of the present invention are, for example, methods for specimen preparation using the composition of the present invention, methods for cyto-pathological, immunocyto-chemical and molecular evaluation of specimens prepared using the composition of the present invention, as well as the equipment and supplies necessary to carry out the specimen preparation, evaluation, or both. In a highly preferred embodiment, the system of the present invention is employed in connection with gynecological testing.

The method of the present invention is particularly useful for stabilizing biological specimens which have been or will be applied to slides for transport and later processing or which will undergo rigorous procedures, such as immunocytochemistry, in situ hybridization and amplification procedures, including RT-PCR, in situ PCR and RT-in situ PCR. The non-crosslinking fixative composition enhances cellular stability, permitting the cells to be stored for longer periods of time without deterioration of morphology, thus increasing accuracy of staining and ease of cytopathologic assessment.

A biological specimen when preserved by the method of the invention can be evaluated using conventional cytologic techniques, even when the specimen is held before staining for at least 45 days. Additionally, a specimen preserved by the method of the invention can be processed for immunocytochemistry and molecular analysis without significant loss or deterioration of the specimen. More particularly, the method of the present invention permits use of a single smear preparation or other type of slide preparation to screen for a number of common pathologies. The time required to process a biological specimen for mounting in paraffin is on the order of several hours as compared with the minutes required to prepare the biological specimen on a slide or other substrate using the stabilizing composition of the invention.

DETAILED DESCRIPTION OF PREFERRED EMBODIMENT

Unless otherwise specified, all percentages herein are by weight. By "optically transparent" as used herein means generally transparent to the naked eye and susbstantially free of opacity. In the context of a biological specimen, one fixed in an optically transparent medium thus allows the visual detail of the specimen to be seen, without substantial interference from opaque fixative artifacts.

Though advantageously employed in such testing, the present invention is not limited to gynecological tests, or for the detection (using conventional methods) of specific diseases such as cancer. It may be adapted and suitably employed in connection with any of a variety of procedures for the preservation or testing of cells, tissues, bodily fluids or other biological specimens. Also, without limitation, specimens prepared in accordance with the present invention are archived and suitably re-used for other tests using conventional test methods, e.g., cytology tests for HPV, HIV, hepatitis (e.g., hepatitis-C) or other disorders. See, e.g., "Use of the Same Archival Papanicolaou Smears for Detection of Human Papillomavirus by Cytology and Polymerase Chain Reaction", by McDonald et al, Diagnostic Molecular Pathology 8(1): 20–25, 1999, hereby incorporated by reference. Thus, the present detailed description is not intended as limiting the scope of the methods, compositions and systems of the present invention.

As used herein, the term "effective amount" refers to an amount sufficient to yield a combination of two or more characteristics of a fixative for a test specimen selected from the group consisting of rapid specimen penetration, minimal specimen shrinkage, protein presentation, antigen preservation, morphology preservation, stain permeability, pathogen-lysis and mixtures thereof. In a highly preferred embodiment, the effective amount is sufficient to yield a combination of all of the immediately preceding disclosed characteristics. Moreover, the effective amount is sufficient to permit effective adhesion to specimen mounting surfaces such as glass slide surfaces. When employing effective amounts of the present composition and its constituent ingredients, use of the composition and system of the present invention thus affords a generally long term record of the specimen, making it attractive for archiving and multiple and archival testing for diagnosis. While specific concentration ranges are provided in the following discussion, by way of illustration, they are not intended as limiting. Moreover, compositions of the present invention may be used in their diluted or concentrate forms.

The composition of the present invention includes, in one preferred embodiment, a first fixative dispersed in a liquid medium. More preferably, the fixative is a chemical fixative. Specifically, the fixatives react chemically (e.g., covalently) with cells and proteins. Still more preferably, it is a chemical fixative known widely in the art as a non-coagulating fixative. Thus, the preferred fixative when contacted with a biological specimen generally will exhibit only insubstantial denaturation (if any) of plasma protein substances in the biological material. It should be realized that in some instances a coagulating fixative may be employed in combination with or a non-coagulating fixative in accordance with certain aspects of the present invention, provided the resulting properties of the overall composition are not materially affected for purposes of handling or later pathological testing. In some instances, a coagulating fixative absent appreciable amounts of non-coagulating fixative may be employed advantageously.

In a highly preferred embodiment, the first fixative is a non-crosslinking chemical fixative, more preferably contains urea, and still more particularly is a diazolidinyl urea (DU), imidazolidinyl urea (IDU), or a mixture thereof. Such fixative is employed in an effective amount as discussed above. By way of illustration, without limitation, the fixative is employed in an amount greater than zero and up to at least its saturation limit (of course, supersaturated amounts that yield the desired characteristics would still fall within the scope of the present invention). Thus, if DU is employed in a generally non-aqueous solvent (e.g., alcohol, as will be discussed in greater detail), the amount of DU preferably ranges up to about 5% and still more preferably, it is about 3% of the composition.

As indicated, the first fixative is dispersed (e.g. dissolved) or otherwise suspended in a liquid medium to form a liquid composition. The liquid medium selected preferably is such that the overall liquid composition exhibit a viscosity that permits it to be applied to a substrate along with a biological specimen so that the liquid composition forms a thin film that fixes the biological specimen and maintains it static. Though the liquid composition may be applied using any suitable method, such as by brush, swab, dropper, pouring, immersion, roller, sponge, dropper, or the like, in a highly preferred embodiment, it is sprayed, such as with a pump spray bottle, or another suitable spraying device (e.g., by aerosol can, compressed gas delivery, etc.). In one preferred embodiment, the viscosity of the liquid composition is on the order of that of water at room temperature. Preferably the liquid medium is substantially optically transparent. However, it may include one or more dies, stains or colorants as desired. The preferred liquid composition is a solution of the fixative in a solvent.

The solvent preferably is substantially free of liquids or other agents that, upon drying, have a tendency to exhibit spotting visible to the naked eye, or of such a magnitude that interference would result in the course of optical examination of the specimen (e.g., by the naked eye, optical microscope, electron microscope, or other optical imaging technique). Thus, while the presence of water and other constituents is tolerable in small amounts, the liquid composition is substantially free of material amounts of them.

Preferably the liquid medium is an organic solvent that itself functions as a fixative. The medium preferably has a relatively low boiling point, and thus will tend to evaporate relatively quickly in typical clinical conditions for the preparation of biological test specimens. Examples of one suitable class of solvents include alcohols such as, without limitation, ethyl alcohol, methyl alcohol, isopropyl alcohol, or mixtures thereof. Other alcohols may likewise be used. Moreover, certain other solvents, such as ketones (e.g. acetone) may likewise be employed.

Optionally, the liquid medium includes a second agent for coating the specimen and protecting it. In one preferred embodiment, the second agent is a relatively large molecule organic compound (preferably carrying a charge), and more preferably is a polyol (even more preferably an alkylene polyol). The second agent preferably functions to help spread cells (for a cell specimen) and protect them from the adverse effects of the atmosphere. At the same time, the second agent has a generally glue-like consistency, helps to form a film, and generally will not interfere with the efficacy of any staining step. Still more preferably, the second agent is a polyol, such as (for example, without limitation) glycol, e.g., an alkylene glycol, such as polyethylene glycol, having a molecular weight of about 1000 to about 20,000, and more preferably it is about 1450. The second agent, when employed, is present in an amount of up to about 5%, and more preferably ranges up to about 1% of the overall composition. In another embodiment, the second agent includes a poloxamer (e.g., poly(oxyethylene)-poly(oxypropylene) copolymers), other alkylene polyols (e.g., polypropylene glycol) or other agents such as polyvinylpyrollidone.

In one preferred embodiment, the relative proportions by weight of first fixative to solvent/fixative to second agent is about 0.01 to about 5 parts first fixative: about 60 to about 95 parts solvent/fixative: 0 to about 3 parts second agent. In a still more preferred embodiment, the relative proportions by weight of fixative to solvent to second agent is about 1 to about 3 parts: about 65 to about 75 parts solvent/fixative: 0 to about 1 part second agent.

The skilled artisan will appreciate that other additives or agents may be incorporated as desired in the composition of the present invention and still fall within the scope of the present invention. By way of illustration, without limitation, known mordants, buffers, penetration increasers, osmotically active substances, nuclear detail improvers, and nuclear size increasers, such as addressed in U.S. Pat. No. 5,196,182, hereby expressly incorporated by reference.

Without limitation, examples of suitable mordants are salts with a metal ion having an oxidation state of two or more. Illustrative are zinc, strontium, calcium, barium and chromium salts. One preferred salt is zinc sulfate.

Suitable buffers include alkali metal phosphate salts such as sodium phosphate and potassium phosphate.

Suitable osmotically active substances include, for instance, alkali metal salts such as sodium chloride. In addition, sugars such as polysaccharides, sucrose, glucose and the like may be employed.

Examples of suitable nuclear detail improvers or size increasers include, without limitation, acetic acid and lithium salts such as lithium chloride. Zinc salts such as zinc sulfate not only improve nuclear definition but also improves staining.

Illustrative of substances for increasing the rate of penetration of the fixing agent are dimethylsulfoxide and ethanol.

The resulting pH of the composition (in its liquid state) of the present invention ranges from about −6 to about 9.5 and more preferably about 7 to about 8.5, and still more preferably about 8.

In another aspect of the present invention, there is provided a composition that is contacted with a biological test specimen on a solid support surface. After contacting the test specimen the composition secures the test specimen to the solid support surface, preferably by adhesive forces. The composition, however, to the naked eye will be generally optically transparent and substantially free of crystals. Moreover, the treated specimens will generally be free of substantial amounts of background noise occasioned by the presence of mucus. Specimens treated in accordance with the present invention render useful specimens for rapid and substantially contemporaneous examination. Moreover, such specimens exhibit long term stability (e.g., greater than about 12 weeks) or extended processing times (even under extreme ambient conditions (e.g., ranging from about −80 degrees C. to greater than about 37 degrees C.; high or low humidity; or high wind stress conditions)). Resulting specimens exhibit stable morphologies, cytoplasmic detail and insubstantial lysis. Likewise, staining and adhesive qualities are preserved over time. In turn, the integrity of specimens can be improved, thereby reducing the risk of specimen loss, lysis, hydration and other cellular artifacts that have a tendency to result in a greater potential for accurate and efficient diagnosis.

Test specimens in accordance with the composition, system and method of the present invention may be prepared for examination in any suitable manner using manual, semiautomated and automated techniques. Examples of instruments used for semiautomated and automated techniques include those offered under the designation THIN PREP (by Cytyc Corp.). For instance, in the Cytyc ThinPrep system, cervical specimens are collected with conventional sampling devices and are placed directly into vials containing a predetermined amount (e.g., about 20 mL) of the stabilizing composition of the invention rather than being prepared as smears. The vials are held at ambient temperature until processed according to manufacturers published procedures. Papanicolaou staining and cytologic screening is then performed.

For a manual technique, the skilled artisan will appreciate that the biological test specimen is obtained by swabbing, scraping, cutting or otherwise gathering the biological material from a test subject. For example, with a pap smear, a suitable amount of cells are obtained according to standard protocols. The cells are placed on a solid support or substrate, such as a glass slide, where they are fixed, and may be stained or otherwise treated preparatory to subsequent pathological examination. Any of a number of subsequent pathological examinations might be employed with samples fixed in accordance with the composition, method and system of the present invention. Independent of using the composition of the present invention, the procedures employed generally are within the knowledge of those skilled in the art, and may be found for instance in guidelines published by the NCCLS, such as GP23-A and GP15-A, hereby incorporated by reference.

In one preferred embodiment, the present preferred composition is used in connection with the preservation of Pap smear specimens (preferably for screening for squamous cell carcinoma, e.g., by screening for low-grade squamous intraepithelial lesions, high-grade squamous intraepithelial lesion or carcinoma-in situ, which employs a step of staining the specimen with a suitable stain. By way of example, without limitation, a Papanicolau stain is employed.

The Papanicolaou stain employs a standard nuclear stain: hematoxylin and two cytoplasmic counterstains: OG-6 and EA. (OG-6 stands for orange-G-6 and consists of Orange G stain plus phosphotungstic acid in 95% ethanol; EA is a mixture of Light Green SF Yellowish and Eosin Y; various preparations of EA may include other reagents, e.g., Bismarck brown, phosphotungstic acid, lithium carbonate, and acetic acid).

The Papanicolaou stain technique is a polychrome method designed to exhibit differences in cellular morphology, maturity, and metabolic activity. Of special importance, since the cells in a cytologic smear tend to overlap, is that this stain produces transparent cytoplasm, which allows the examiner to see through layers of cells, debris, and mucus. Different modifications of the classic Papanicolaou stain produce variations in intensity of nuclear and cytoplasmic staining. The choice of which modification to use is largely a matter of personal preference.

The Modified Papanicolaou Staining Procedure ("A Guide to Cytopreparation," Am. Soc. for Cytotechnology) is the currently recommended method for staining gynecologic cytology preparations, especially cervico-vaginal smears, because it provides: (1) well-stained (blue) chromatin and definition of nuclear detail; (2) differential counterstaining (e.g., staining the cytoplasm of different cell types different colors, reflecting the maturity and activity of the cells); and (3) cytoplasmic transparency.

Obtaining a specimen for the gynecologic Pap smear test is done by a health care provider as part of a pelvic examination. Generally, there are five methods of collection of gynecologic material for cytological examination: (1) cervical scrape or smear, (2) aspirate from the posterior fornix, (3) vaginal smear, (4) endocervical canal smear, and (5) endometrial aspirate. Each of these methods is well known in the art. See, e.g., Bourne, L. D. (1990), *Theory and Practice of Histological Techniques,* "Gynaecological Cytology," Church Hill Livingstone, Edinburgh; Allen, *A Guide to Cytopreparation,* Am. Soc. for Cytotechnology, hereby incorporated by reference. Cells are collected, transferred onto a glass slide and immediately fixed, and sent to the laboratory for staining and examination under a microscope. A cytotechnologist examines the smear microscopically for the presence of abnormal cells.

In another aspect of the present invention, it is contemplated that the composition of the present invention is provided as part of a kit that may include one or more additional materials or instruments selected from stain, dye, immunostain, slide, coated glass slide (e.g., albumin, water-soluble glue, chrome alum, or poly-L-lysine, activated glass slide (e.g. treated with a silane such as aminoalkylsilane) scalpel, swabbing, pipette, reference control, storage rack, storage container, transport container, data forms, labelers or coverslips.

Likewise, it is contemplated that the composition of the present invention is provided with one or more semi-automated or automated instruments, such as instruments for staining, coverslipping, slide or substrate preparation or the like. In yet another embodiment, it is contemplated that the composition, method and system of the present invention is employed with an optical microscope, an electron microscope, or some other optical imaging instrument; some or all of these may further include a computerized workstation with readout and printout devices associated with them. In other instances, it may be possible to employ flow cytometry or cell culture analysis to specimens treated in accordance with the present invention. Thus, the present invention may be advantageously employed in connection with many cytological, immunochemical and molecular diagnostic applications. Examples of particularly preferred instruments include, without limitation, AUTO PAP (by NeoPath) and PAPNET (by Neuromedical Systems), which are automated slide scanning systems. Other complementary systems that may be employed include those having the designation AcCELL and TracCELL (by AccuMed), and SCREEN (by AutoCyte)

The composition of the present invention may be prepared in any suitable manner. In one highly preferred embodiment, where the first fixative includes DU, about 3 parts by weight (15 g) of the DU is first dissolved in 30 parts water (which may be at room temperature)(150 ml). The DU/water solution is then diluted to to about 70 parts by weight alcohol (350 ml). For example, where the solvent is isopropyl alcohol, about 99% isopropyl alcohol is added, along with about 0.05 parts of polyethylene glycol (0.25 g). The resulting formulation exhibits a pH in the range of about 7.8 to about 8.2. Optionally it has a concentrated osmolarity calculated to about 250 to about 500 (e.g. about 290). It is filtered through a 0.8 um bottle-top filter and then a 0.2 um bottle-top filter and placed into a suitable delivery device, such as a 35 ml fill spray bottle.

By way of illustration, and without intending to be limited thereby, the following illustrates various protocol that may be suitably employed in the present invention.

EXAMPLE 1

In a first illustration, an immunocytochemistry procedure is performed, where slides smeared with cervical samples are sprayed (e.g. 2–3 pumps) with the composition of the present invention, and allowed to dry. The slides are gently rinsed with PBS (phosphate buffered saline) and incubated with about 0.3% hydrogen peroxide in PBS for about 30 minutes to help block endogenous peroxidase activity. Excess peroxide is drained from the slide and the slides are washed three times over 5 minutes with PBS. Excess PBS is drained from the slide. The slides are then incubated with either 5% bovine serum albumin (BSA) in PBS or 10% normal goat or rabbit serum for about 30 minutes at about 37 degrees C. in a humidified chamber, and then rinsed three times in PBS (2 minutes each). The excess is drained.

The primary antibody is applied (biotin labeled anti-HPV Type 16) directly on the slide in the appropriate dilution to cover the specimen, e.g., about 400 uls, and allowed to incubate about 1 hour at room temperature or about 30 minutes in a humidified chamber. Excess antibody is drained off and the slides are then washed three times in PBS (2 minutes each).

A suitable conjugated enzyme, e.g., HRP (horseradish peroxidase) Streptavidin conjugate is added and incubated for 30 minutes at room temperature. The sample is washed three times in PBS and the excess is drained.

About 400 ul (microliters) of the peroxidase substrate (e.g., DAB) is added and allowed to incubate for about 5 minutes. After incubation and development, the excess is drained and the sample is washed three times in PBS then three times in distilled water. The excess wash is drained.

The smear is then counterstained (e.g., in Meyer's hematoxylin for about 2–10 minutes), and the slide is submerged in about 30 mM ammonium hydroxide for about 15 seconds followed by a brief water rinse. Slides are coverslipped with an aqueous mounting media and successfully examined microscopically.

EXAMPLE 2

In another illustration, in situ hybridization is performed. In this illustration, slides smeared with cervical samples are sprayed with the composition of the present invention (2 to 3 pumps). About 400 ul of a hybridization cocktail is applied to the slide (2×SSC, 10% dextran sulfate, 2×Denhard's Solution, 50% formamide, 200 ug(micrograms)/ml denatured herring sperm DNA). The slide is coverslipped and incubated at about 37 degrees C. in a humidified chamber.

Excess cocktail is drained from the slide and it is blotted dry.

Biotinylated probe (HPV 16 consensus probe) is added to the hybridization cocktail (about 0.5 to about 2 ng/ul) and about 100 ul of the cocktail is added to the slide. The slide is coverslipped and allowed to denature at about 95 degrees C. for about 2 minutes in a humidified chamber. The slides are transferred to a 37 degree humidified chamber and incubated for about 1–2 hours (or optionally overnight at about 4 degrees C.)

The coverslip is removed and the sample is washed in a buffer, e.g., 2×SSC (sodium chloride-sodium citrate) buffer pre-warmed to about 60 degrees C. for about 5 minutes. The slide is then washed in a buffer such as 2×SSC buffer at room temperature for about 5 minutes and the excess buffer is shaken off.

The slide is blocked with blocking solution (e.g., 0.5% BSA in TBS (tris-buffered saline)) for 10 minutes and the excess drained.

The sample is then incubated with a conjugated enzyme (e.g., HRP-Streptavidin conjugate) for about 20 minutes at room temperature in a humidified chamber. it is then washed three times in about 0.02–0.05% v/v Tween-20 in TBS over about 5 minutes.

About 400 ul of the peroxidase substrate (e.g.,DAB (diaminobenzadine)) is added and allowed to incubate for about 5 minutes. After incubation and development, the excess is drained and the sample is rinsed three times in PBS and then three times in distilled water. The excess wash is drained.

The smear is counterstained in Meyer's Hematoxylin for about 2–10 minutes and the slide is submerged in about 30 mM ammonium hydroxide for about 15 seconds followed by a brief water rinse.

The slides are coverslipped with an aqueous mounting medium and successfully examined microscopically.

Liquid-based collection procedures are employed as an alternative to the slide smear technique, and yields like results. With these methods, sampling instruments are rinsed in a fixing solution in accordance with the present invention, which is then sent to the laboratory.

EXAMPLE 3

A sample of cells is obtained from the cervix to screen for cervical cancer, its precursors, and other abnormalities of the reproductive tract. The specimen includes samples of the squamous and columnar epithelium, encompassing in particular the transformation zone where the majority of cervical neoplasias appear. The cellular material that is collected is applied to a glass slide, and quickly but evenly spread the cellular material in a thin layer on the glass slide. Large clumps of material are thinned out as much as possible, while avoiding excessive manipulation which can damage cells. To avoid developing air-drying artifacts, therefore, the material is transferred from the sampling instrument to the slide within a few seconds and immediately fixed using the composition of the present invention. The fixed specimen is dried, and prepared for transporting or storing. The specimen is fixed to the slide by either immersing in the fixative or coating the slide with a surface fixative, which typically includes polyethylene glycol (PEG). Spray-fixed or liquid-coated slides are allowed to dry completely before packaging for transportation or staining specimens prepared are successfully examined.

EXAMPLE 4

Approximately 50 sets of slides (two prepared Pap Smear slides per patient, per set) are taken from 50 randomly selected patients for a split-specimen study. Each slide includes an endocervical and ectocervical smear specimen. One slide is sprayed with the composition of the invention and the other was sprayed with a conventional aqueous alcohol buffer solution fixative for slide preparations (i.e., SURGIPATH), for comparison. For each of the patient slide sets, at the time of collection, the health care provider sprays the slides, and documents, numbers and labels each slide as A or B, indicating whether the slide is sprayed with the composition of the present invention (A) or the conventional fixative (B). Each slide set is numbered and matched to the patient case history, pathology report and scoring report forms.

The specimens are processed as obtained using the modified Papanicolaou staining procedure. The sets of slides are stained in tandem and read by a panel of pathologists who score and evaluate each slide (both ectocervical and endocervical smears) for a number of parameters, including a readable diagnosis and ASCUS (atypical squamous cells of undetermined significance) determination, cell morphology, nuclear and cytoplasmic staining detail, staining intensity and preservation quality. Table I provides the qualitative results, where the "same, better or worse" descriptions refer to the relative observable differences between A and B (e.g., a score of "better" means that the composition of the present invention fared better than the conventional fixative).

TABLE I

| Characteristic Observed | Better | Same | Worse |
| --- | --- | --- | --- |
| Squamous Cell Preservation | 6 | 42 | 2 |
| cellular morphology | | | |
| nuclear detail | | | |
| cytoplasmic detail | | | |
| Squamous Cell Stain Quality | 7 | 39 | 3* |
| nuclear and cytoplasmic | | | |
| Overall Endocervical Cell Preservation | 5 | 44 | * |
| (columnar and metaplastic) | | | |
| cellular morphology | | | |
| nuclear | | | |
| cytoplasmic | | | |
| Endocervical Cell Stain Quality | 7 | 42 | * |
| nuclear and cytoplasmic | | | |
| Overall Slide Quality | 7 | 39 | 4 |
| background | | | |
| organisms** | | | |
| Diagnosis | 3 | 46 | 1 |
| similar diagnosis | | | |
| ease of diagnosis | | | |
| ASCUS determination | | | |

*only 49 subjects are considered; one has history of previous hysterectomy.
**mucous, HPV, HSV, Doberlien bacteria, yeast, other bacterial or specific complications.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A method for preserving a biological test specimen to screen for multiple assays, comprising the steps of:
    a) spraying a biological test specimen that has been placed on a solid support surface, after being placed thereon, with an effective amount of a fixative composition, said fixative composition including a urea fixative dispersed in a solvent that is substantially free of water; and
    b) evaporating said solvent to yield an optically transparent fixative for preserving said biological test specimen and adhesively securing said biological test specimen to said solid support surface for pathological examination of said specimen while on said solid support surface; and
    c) screening said secured test specimen for cancer and for at least one disorder selected from HIV, HPV or hepatitis.

2. A method according to claim 1 wherein said fixative includes diazolidinyl urea.

3. A method according to claim 2 wherein said diazolidinyl urea is present in an amount up to about 5% of said composition.

4. A method according to claim 3 wherein said diazolidinyl urea is present in an amount of about 3% of said composition.

5. A method according to claim 1 wherein said composition further comprises a polyol.

6. A method according to claim 5 wherein said composition further comprises a glycol.

7. A method according to claim 6 wherein said composition further comprises polyethylene glycol.

8. A method according to claim 1 wherein said composition includes diazolidinyl urea in an amount up to about 5%, a glycol in an amount up to about 5%, and an alcohol.

9. A method according to claim 1 wherein said composition upon drying on a carrier is substantially free of crystallines to the naked eye.

10. A method according to claim 1 further comprising providing a gynecological test specimen from a pap smear test.

11. A method according to claim 1 further comprising conducting a pathological examination of a gynecological test specimen after it has been fixed with said composition.

12. The method of claim 1, wherein said screening includes immunocytochemical staining.

13. The method of claim 1, wherein screening includes in situ hybridization.

14. The method of claim 1, wherein screening includes in situ amplification.

15. The method of claim 1, wherein screening includes fluorescent in situ hybridization.

16. A method for preserving a gynecological test specimen to screen for multiple assays, comprising the steps of:
   a) spraying, on a solid support surface, a gynecological test specimen with a composition including:
      1) diazolidinyl urea; and
      2) an alcohol solvent,
   b) drying said solvent to yield an optically transparent fixative for preserving said gynecological test specimen and adhesively securing said biological test specimen to said solid support surface for pathological examination while on said solid support surface; and
   c) screening said secured test specimen for cancer and for at least one disorder selected from HIV, HPV or hepatitis.

17. A method according to claim 16 wherein said diazolidinyl urea is present in an amount up to about 5% of said composition.

18. A method according to claim 17 wherein said diazolidinyl urea is present in an amount of about 3% of said composition.

19. A method according to claim 16 wherein said composition further comprises a polyol.

20. A method according to claim 19 wherein said composition further comprises a glycol.

21. A method according to claim 20 wherein said composition further comprises polyethylene glycol.

22. A method according to claim 16 wherein said composition includes diazolidinyl urea in an amount up to about 5%, a glycol in an amount up to about 5%, and an alcohol solvent.

23. A method according to claim 16 further comprising providing said gynecological test specimen from a pap smear test.

24. A method according to claim 16 wherein said composition upon drying on a substrate is substantially free of crystallines to the naked eye.

25. The method of claim 16, wherein said screening includes immunocytochemical staining.

26. The method of claim 16, wherein screening includes in situ hybridization.

27. The method of claim 16, wherein screening includes in situ amplification.

28. The method of claim 16, wherein screening includes fluorescent in situ hybridization.

29. A method for preserving a biological test specimen to screen for multiple assays, comprising the steps of:
   a) transferring a biological test specimen from a sampling instrument to a glass slide;
   b) immediately contacting said biological test specimen on said glass slide with an effective amount of a fixative composition, said fixative composition including:
      1) diazolidinyl urea; and
      2) an alcohol solvent; and
   c) evaporating said solvent to yield an optically transparent fixative film for preserving said biological test specimen and adhesively securing said biological test specimen to said solid support surface for microscopic pathological examination of said specimen while on said glass slide; and
   d) further screening said secured test specimen for cancer and for at least one disorder selected from HIV, HPV or hepatitis.

30. The method of claim 29, wherein said screening includes immunocytochemical staining.

31. The method of claim 29, wherein screening includes in situ hybridization.

32. The method of claim 29, wherein screening includes in situ amplification.

33. The method of claim 29, wherein screening includes fluorescent in situ hybridization.

34. A method for preserving a gynecological test specimen to screen for multiple assays, comprising the steps of:
   a) transferring a gynecological test specimen from a sampling instrument to a glass slide;
   b) immediately contacting said gynecological test specimen on said glass slide with an effective amount of a fixative composition, said fixative composition including:
      1) up to about 5% of diazolidinyl urea;
      2) up to about 5% of a polyol; and
      3) an alcohol solvent; and
   c) evaporating said solvent to yield an optically transparent fixative film for preserving said gynecological test specimen and adhesively securing said gynecological test specimen to said solid support surface for microscopic pathological examination of said specimen while on said glass slide; and
   d) conducting a Pap smear analysis of said secured gynecological test specimen; and
   e) further screening said gynecological test specimen for at least one additional disorder selected from HIV, HPV or hepatitis.

* * * * *